United States Patent
McGaffigan

(10) Patent No.: US 6,551,300 B1
(45) Date of Patent: Apr. 22, 2003

(54) DEVICE AND METHOD FOR DELIVERY OF TOPICALLY APPLIED LOCAL ANESTHETIC TO WALL FORMING A PASSAGE IN TISSUE

(75) Inventor: Thomas H. McGaffigan, Saratoga, CA (US)

(73) Assignee: Vidamed, Inc., Minneapolis, MN (US)

( * ) Notice: Subject to any disclaimer, the term of this patent is extended or adjusted under 35 U.S.C. 154(b) by 35 days.

(21) Appl. No.: 09/680,388

(22) Filed: Oct. 4, 2000

(51) Int. Cl.[7] ............................................. A61M 31/00
(52) U.S. Cl. ....................................... 604/500; 604/265
(58) Field of Search ............................... 604/500, 502, 604/96, 49, 264, 265

(56) References Cited

U.S. PATENT DOCUMENTS

| | | | |
|---|---|---|---|
| 4,550,126 A | | 10/1985 | Lorenz |
| 5,389,074 A | | 2/1995 | Parker et al. |
| 5,417,671 A | * | 5/1995 | Jackson ...................... 604/265 |
| 5,558,642 A | | 9/1996 | Schweich, Jr. et al. |
| 5,810,786 A | * | 9/1998 | Jackson et al. ............. 604/265 |
| 5,843,033 A | | 12/1998 | Ropiak |
| 5,871,475 A | * | 2/1999 | Frassica ...................... 604/264 |
| 5,895,375 A | | 4/1999 | Wilcox et al. |
| 5,906,587 A | * | 5/1999 | Zimmon ...................... 604/49 |
| 6,004,290 A | * | 12/1999 | Davis .......................... 604/96 |
| 6,183,461 B1 | * | 2/2001 | Matsuura et al. ........... 604/502 |

OTHER PUBLICATIONS

Author Unknown, Urology Product Tour, "Bard Foley Catheters" website article located at: *http://www.bardmedical-.com/urology/cathtour.html,* printed on (Sep. 6, 2001), 2 pgs.

Author Unknown, "history of IMS", website located at *http://www.ims–limited.com/history.html,* printed on (Sep. 5, 2001), 2 pp.

Milton I. Houpt, et al., "Lidocaine Reducing Pain", Compendium, (Apr. 1997) vol. 18, No. 4, 6 pgs.

Author Unknown, Urology Product Tour, "Tour the Bardex I. C. Catheter", website located at *http://www.bardmedical-.com/urology/catheter/2way.html,* printed on (Sep. 6, 2001), 1 pg.

Author Unknown, "Story of Lidoderm", website located at *http://www.lidoderm.com/Story doctors.html,* printed (Sep. 5, 2001), 8 pgs.

S.D. Madduri, "Madduri Urethrogram Catheter" Ureteral and Urethral Catheters, p. 33, Sold at least as early as (Dec. 31, 1998), 1 pg.

Author Unknown, "MEDICELL Medical Foams" 1 pg.

Author Unknown, AVITAR "Custom Foam Products", website located at *http://www.avitarinc.com/custom foam products.html,* printed on (Sep. 18, 2001), 2 pgs.

* cited by examiner

*Primary Examiner*—Teresa Walberg
*Assistant Examiner*—Leonid Fastovsky
(74) *Attorney, Agent, or Firm*—Dorsey & Whitney LLP

(57) ABSTRACT

A device for delivering a topically applied anesthetic agent gel to a wall forming a passage in tissue comprising a flexible elongate cylindrical member having proximal and distal extremities. The member is sized so that it can be inserted into the passage. An anesthetic agent is carried by the member for supplying the anesthetic agent along at least the distal extremity of the member for a sufficient period of time to anesthetize the wall and the tissue surrounding the wall whereby other medical devices can be inserted into the passage without substantial pain to the patient.

21 Claims, 4 Drawing Sheets

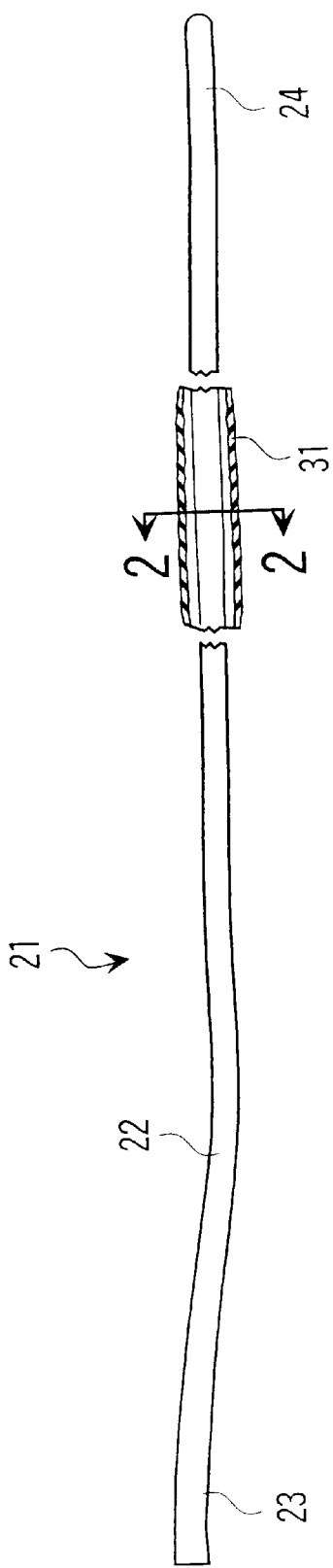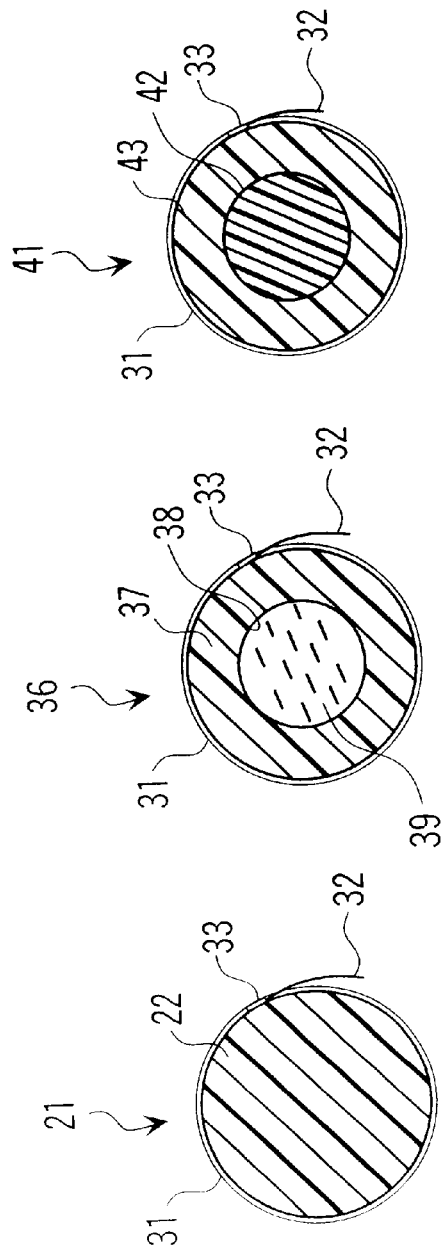

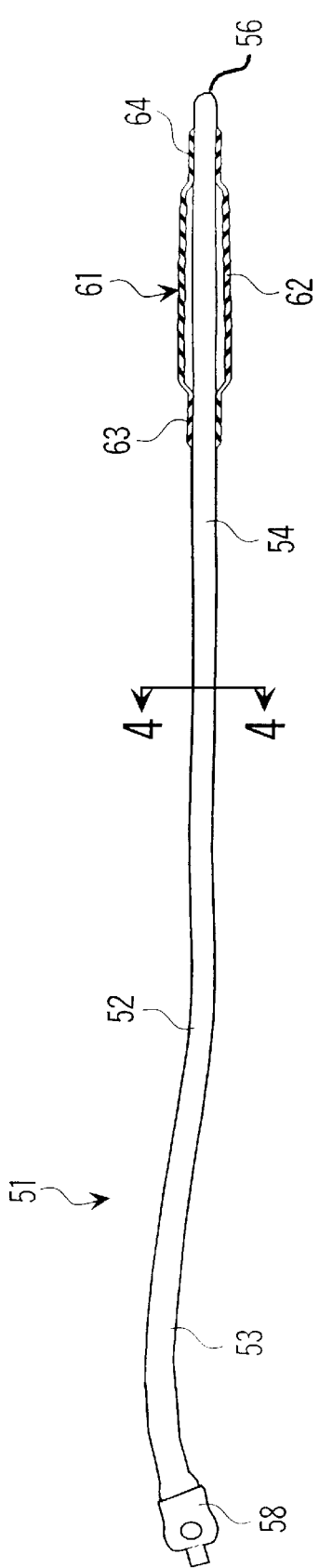
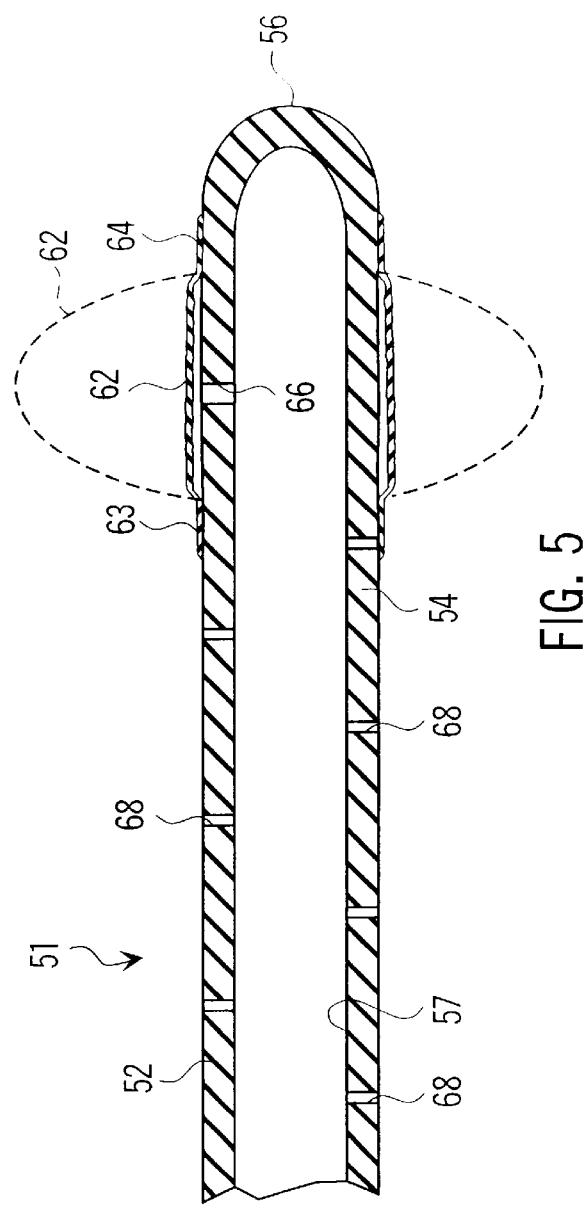
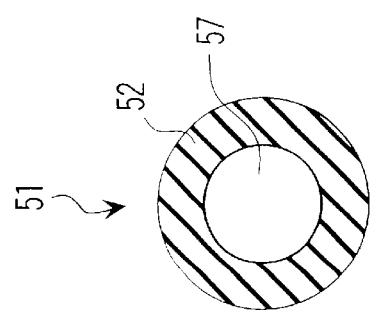
FIG. 3
FIG. 4
FIG. 5

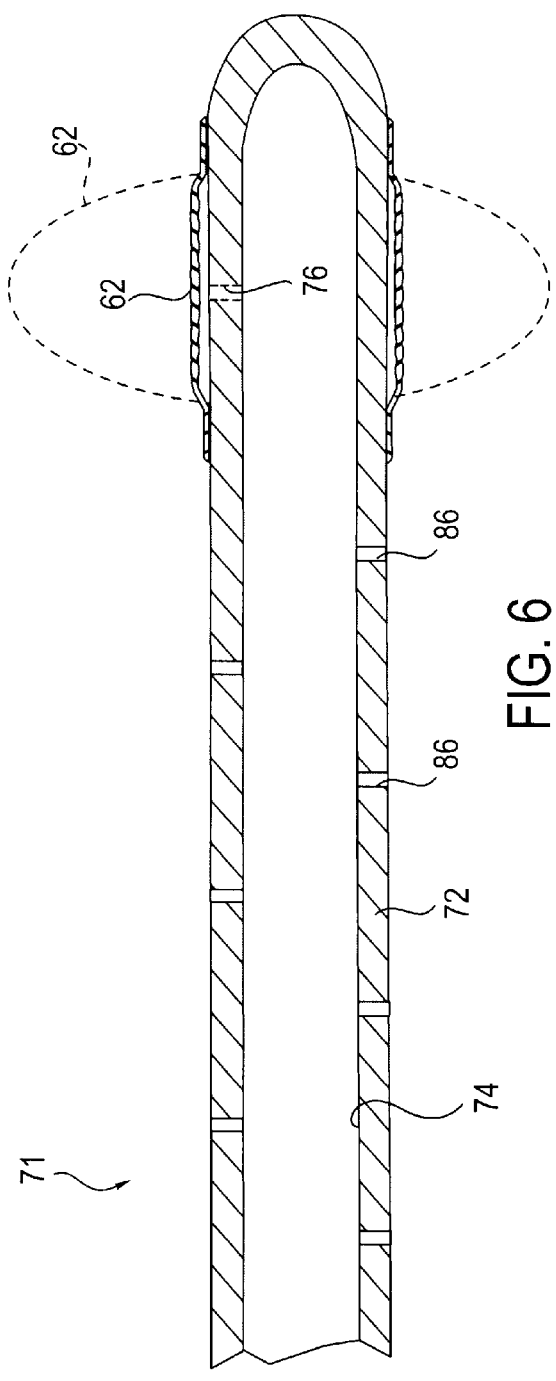
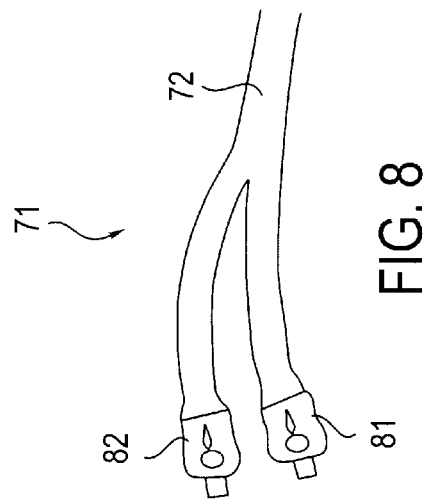
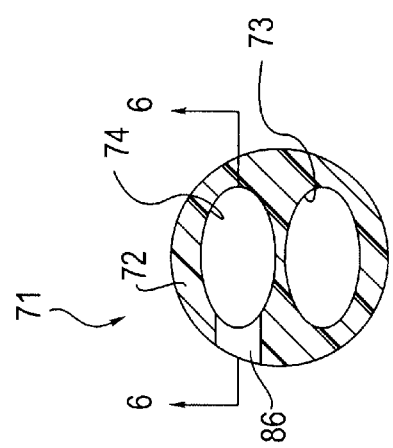

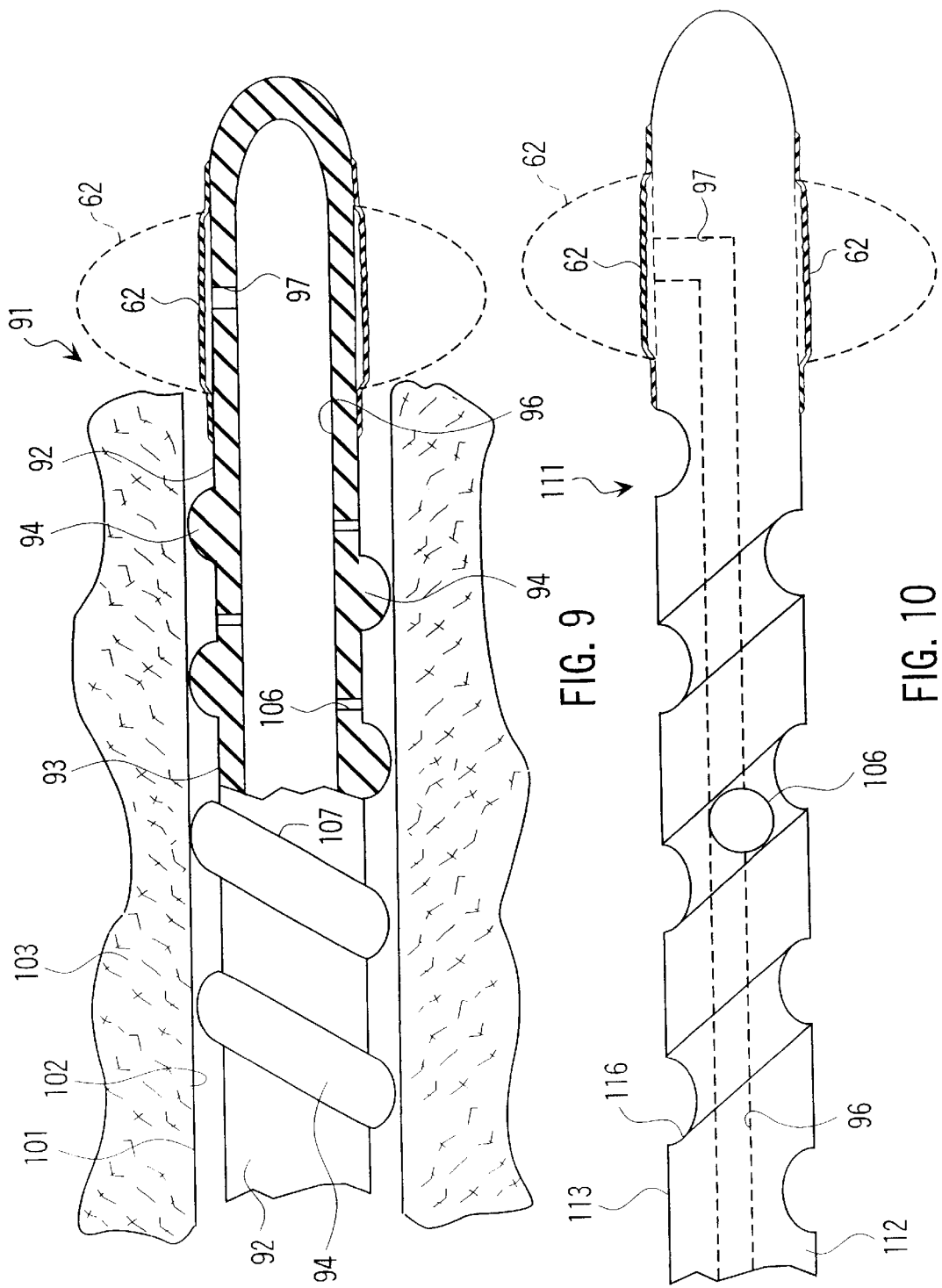

DEVICE AND METHOD FOR DELIVERY OF TOPICALLY APPLIED LOCAL ANESTHETIC TO WALL FORMING A PASSAGE IN TISSUE

This invention relates to an device and method for delivery of topically applied local anesthetic to wall forming a passage in tissue.

In certain medical procedures as for example the treatment of BPH by a TUNA procedure of Vidamed, Inc. which utilizes a cylindrical probe inserted into the urethra of the penis after typically a lidocaine jelly has been introduced into the urethra by a syringe and clamping the end of the penis to retain the lidocaine jelly in the penis for a predetermined period of time, it has been found in at least some cases that such an application of lidocaine jelly is ineffective. This is believed to possibly be caused by constrictions in the urethra and also because there is no mechanism for preventing the lidocaine placed in the urethra from leaking into the bladder. There is therefore a need for a device and method for overcoming these difficulties.

In general, it is an object of the present invention to provide a device and method for delivery of a topically applied local anesthetic agent in a desired location of a wall forming a passage in tissue.

Another object of the invention is to provide a device and method of the above character particularly suitable for use in the urethra of the human male.

Another object of the invention is to provide a device and method of the above character which makes it possible to retain the anesthetic agent in the urethra without leaking into the bladder for a predetermined period of time.

Another object of the invention is to provide a device and method of the above character which ensures that the anesthetic agent is substantially uniformly distributed along the length of the passage in which the device is disposed.

Another object of the invention is to provide a device and method of the above character in which a continuous supply of anesthetic agent is provided.

Another object of the invention is to provide a device and method of the above character which can be readily used.

Another object of the invention is to provide an apparatus which can be economically manufactured.

Additional objects and features of the invention will appear from the following description in which the preferred embodiments are set forth in detail in conjunction with the accompanying drawings.

FIG. 1 is a side elevational view of a catheter-type device incorporating the present invention and utilized in performing the method of the present invention.

FIG. 2 is an enlarged cross sectional view taken along the line 2—2 of FIG. 1.

FIG. 2A is a view similar to FIG. 2 but showing an alternative embodiment of the catheter-type device shown in FIG. 1.

FIG. 2B is another view similar to FIG. 2 but showing still another embodiment of a catheter-type device shown in FIG. 1.

FIG. 3 is a side elevational view of another catheter-type device incorporating the present invention.

FIG. 4 is a cross sectional view taken along the line 4—4 of FIG. 3.

FIG. 5 is a sectional view of the distal extremity of the catheter-type device shown in FIG. 3.

FIG. 6 is a sectional view, taken along the line 6—6 of FIG. 7, similar to FIG. 5 but showing an alternative embodiment of a catheter-type device.

FIG. 7 is a cross sectional view of the catheter-type device of FIG. 6.

FIG. 8 is a side elevational view of the proximal extremity of the catheter-type device shown in FIG. 6.

FIG. 9 is another sectional view partially in section showing another embodiment of a catheter-type device incorporating the present invention.

FIG. 10 is side elevational view of another embodiment of a catheter-type device incorporating the present invention.

In general, the device for applying a topically applied local anesthetic agent into the wall forming a passage in tissue comprises a flexible elongate cylindrical member having proximal and distal extremities and having an outer surface extending from the proximal extremity to the distal extremity. The cylindrical tubular member is sized so that it can be introduced into the passage and retained in the passage for a predetermined period of time. Means is carried by the cylindrical tubular member for delivering an anesthetic agent to the wall forming the passage.

More in particular, a device 21 incorporating the present invention is shown in FIGS. 1 and 2 for delivery of a topically or surface applied anesthetic agent which can be in the form of a liquid including a viscous liquid such as a gel. The device 21 consists of a flexible elongate cylindrical member 22 having proximal and distal extremities 23 and 24. As shown in FIG. 2, the member 22 is a solid member and is formed of a suitable medical grade open cell plastic foam. The open cell foam material can be custom molded. The foam material can be of a type such as supplied by Avitar, Inc., 65 Dan Road, Canton, Mass. 02021. Such forms are hydrophilic and can retain as much as many times their weight in liquid and gels. Such foam materials are also available from Hydromer, Inc., 35 Industrial Parkway, Branchburg, N.J. 08876. Such hydrophilic foams typically are made of a polyurethane and polyvinyl pyrrolidone polymers. These foams are two component, chemically frothed, open cell systems which exhibit high absorptivity and tensile strength as well as softness. Such foams are available in cell sizes ranging from 500 to 200 cells per inch. Such cell foams can provide a uniform dispersion of additives such as an anesthetic agent utilized in the present invention. The anesthetic agent can be in the form of any anesthetic which can be topically applied as for example lidocaine or Zylocaine or a combination of lidocaine and Zylocaine. The use of such a foam is particularly desirable because the foam provides superior absorbency and effectively provides a controlled release of anesthetic liquids such as gels for topical or surface applications as in the present invention.

The member 22 for use in the male urethra would have a diameter ranging from 4 to 7 millimeters and preferably approximately 5 millimeters. The member would have a suitable length as for example 10 to 15 inches and preferably approximately 12 inches. The distal extremity 24 is provided with a rounded hemispherical tip 26 to facilitate insertion of the device into the male urethra. The member 22 should have sufficient stiffness so that it can be progressively pushed into the male urethra until it reaches the bladder.

The foam material comprising the member 22 is impregnated with an anesthetic agent typically in a gel for as for example an anesthetic agent gel which is a gel of hydroxypropyl methyl cellulose containing approximately 5% anesthetic agent. The impregnation can be carried out by way of example by placing the member 22 in an anesthetic agent bath at room temperature under a pressure of 100 psi for a period of 5 minutes to ensure that the gel has been introduced throughout the foam of the member 22 and distributed uniformly at least through the distal-most 6 to 8 inches of the member 22. It should be appreciated that it is also possible to utilize anesthetic agents which are incorporated in a material which is a liquid at room temperature but which becomes a gel at body temperature of 98.6° F. Such an anesthesia has been identified as a 4% thermosetting gel. The use of a gel is advantageous because the gel ensures that the anesthesia will remain in location.

In order to retain the anesthetic gel impregnated within the member 22, a release liner 31 formed of a suitable impervious plastic circumscribes the member 22 and extends the length of the member 22. The liner 31 is provided with a flap 32 which is adjacent to an overlap 33 of the release liner 31 which is sealed in this region by way of example by the use of an adhesive (not shown). The flap 32 is free so that it can be readily grasped by the fingers of a human hand to aid in stripping the liner from the member 22 when it is desired to utilize the device 21 as hereinafter described.

Operation and use of the device 21 in performing a medical procedure may now be briefly described as follows. Let it be assumed that the patient is a human male having a bladder emptying through the urethra in the penis and in which the urethra is formed by a wall surrounded by tissue. The urethra is surrounded by the prostate gland adjacent the bladder. The penis is provided with a penile shaft with a glans at its outermost extremity.

Let it be assumed that the patient is to be treated for BPH by the use of a TUNA procedure, a transurethral needle ablation procedure utilizing a TUNA device of the type supplied by Vidamed, Inc. of Fremont, Calif. Such a device includes a needle carrying probe having a diameter ranging from 18 to 23 French. In preparing the patient for introduction of the probe of the device into the urethra, it is desirable to introduce an anesthetic agent which can be topically applied. In connection with the present invention this is accomplished after the patient has been prepared for the TUNA procedure by removing the device 21 from its packaging and thereafter stripping away the release liner 31 from the flexible elongate cylindrical member 22. The physician then grasps the distal extremity 24 of the member 22 of the device 21 and inserts it into the urethra of the penis and progressively advances it into the penis for a sufficient distance to ensure that the distal extremity 24 extends beyond the prostate gland. The member 22 is left in place for a predetermined period of time as for example approximately 15 minutes, during which time the anesthetic agent gel within the member oozes out into contact with the wall forming the urethra and thereafter continuously applies anesthetic agent gel to the wall to locally anesthetize the wall and the tissue surrounding the wall. After the predetermined time, the member 22 can be removed from the urethra and the device 21 discarded. Thereafter, the physician can continue with the TUNA procedure in a conventional manner.

By the use of the device 21, the physician is ensured that anesthesia is supplied along the entire length of the urethra and particularly in the area of the prostate gland. This ensure that the patient will be able to endure the insertion of the probe of the TUNA device in all cases during the TUNA procedure and to thereby make it possible to perform such TUNA procedures in out-patient facilities.

Another device incorporating the present invention is device 36 as shown in FIG. 2A in which there is also provided a flexible elongate cylindrical member 37 having generally the same conformation as the device 21 in length, size, etc. The member 37 is also formed of a medical grade open cell plastic foam material but is also provided with a centrally disposed storage lumen 38 extending the length of the member 37 from the proximal extremity to the distal extremity. An anesthetic agent gel 39 fills the lumen 38 to ensure that the foam material of the member 37 is impregnated with the anesthetic agent gel and also to provide an additional supply of the anesthetic agent gel during use of the device. The member 37 is sealed by the release liner 31 of the type hereinbefore described in conjunction with FIGS. 1 and 2. The device 36 can be utilized in the same manner as that described for the device 21 in FIGS. 1 and 2.

When it is desired to provide a device of the present invention having additional stiffness, a device 41 as shown in FIG. 2B can be utilized. The device 41 consists of a stiffening member 42 formed of a solid medical grade plastic as for example a polyurethane or Teflon. The stiffening member can extend substantially the entire length of the device 41 from the proximal extremity to the distal extremity. The stiffening member 42 can be formed of the desired stiffness to facilitate insertion of the device into the urethra. The stiffening member is covered with a cylindrical tubular member 43 formed of an open cell foam material of the type hereinbefore described and also extending the length of the device. This foam material is impregnated with an anesthetic agent gel in the same manner as the member 22 device 21. The member 43 is covered with a release liner 31 of the type hereinbefore described. The device as shown in FIG. 2B can be utilized in the same manner as the devices 21 and 36 hereinbefore described with the additional advantage that it is provided with additional stiffness when that is needed to facilitate insertion of the device into a passage as for example the male urethra.

Another device incorporating the present invention is devices 51 shown in FIGS. 3, 4 and 5. As shown therein, the device 51 consists of a flexible elongate tubular member 52. The tubular member 52 is provided with proximal and distal extremities 53 and 54. The member 52 can be of a suitable size as for example a diameter of 12 French corresponding to 5 millimeters and having a length ranging from 10 to 18 inches and preferably a length of approximately 15 inches. The member 52 is formed of a suitable medical grade material as for example latex rubber, silicone rubber or fluoroelastomers. The distal extremity 54 is provided with a rounded hemispherical tip 56. The member 52 is provided with a lumen 57 extending from the tip 56 the distal extremity 54 to the proximal extremity 53 and extends through a Luer type fitting 58 mounted on the proximal extremity and adapted to receive a conventional syringe. The member 52 has a wall thickness of approximately ½ millimeter.

Anchoring and sealing means 61 is provided on the distal extremity 54 immediately proximal of the tip 56 and takes the form of an inflatable and deflatable elastomeric balloon 62. The balloon 62 is provided with proximal and distal extremities 63 and 64 which are bonded to the outer surface of the distal extremity of the flexible elongate tubular member 52 by suitable means such as an adhesive. The extremities 63 and 64 are positioned in such a manner so that when the balloon 62 is inflated as hereinafter described, the distal extremity of the balloon 62 is just proximal of the tip 56. A balloon inflation lumen 66 which is in communication with the lumen 57 extends into the balloon 62 for inflation and deflation of the balloon.

A plurality of longitudinally and circumferentially spaced apart ports 68 are provided proximal of the balloon 62 and extend proximally for a distance as for example approximately 5 inches, an appropriate length for the treatment of the male urethra. However, it should be appreciated that in accordance with the present invention fewer or less ports opening into the central lumen 57 can be provided depending upon the application of the device. The ports 68 can have a suitable diameter as for example 2 to 3 millimeters. Some patients experience discomfort at the tip of the penis and therefore it is desirable to have ports which are spaced so that at least one port is disposed in the tip of the penis. The number of the ports and spacing of the ports can be varied in accordance with the desired flow rate of the anesthetic agent gel along the length of the device.

Operation and use of the device 51 is similar to that hereinbefore described with respect to the devices 21, 31 and 41. Let it be assumed that it is desired to perform a TUNA procedure on a male patient. The device 51 is unpackaged and is covered with a lubricant as for example a lidocaine gel over its entire length. A conventional syringe as for example a 30 milliliter syringe (not shown) filled with the anesthetic agent gel is attached to the fitting 58. The physician inserts the tip 56 of the device 51 into the urethra of the penis and progressively advances the member 52 for a sufficient distance to ensure that the balloon 62 on the distal extremity is disposed within the bladder of the patient. The physician then operates the syringe to cause anesthetic agent gel to enter the lumen 57 and to pass through the inflation port 66 to inflate the balloon 62 to a suitable diameter as for example by introducing 5 cc's of the anesthetic agent gel into the balloon 62. As soon as the balloon 62 has been inflated, the physician or urologist pulls proximally on the member 52 to pull the inflated balloon 62 against the urethral opening in the bladder neck. The fitting 58 contains a check valve of a suitable type as for example a duckbill type valve so that the balloon 62 remains inflated. The inflated balloon 62 when positioned in this manner serves to seal the urethral passage from the bladder and serves to prevent the leakage of anesthetic agent gel from the urethra into the bladder. After insertion of the device, a conventional clamp (not shown) is placed on the glans to clamp the penis and to seal it against the catheter.

The anesthetic agent gel during inflation of the balloon and after inflation of the balloon passes through the ports 68 to disperse the anesthetic agent gel uniformly along the urethra wall to anesthetize the wall and surrounding tissue. Thus, it can be seen that the balloon 62 as it deflates also serves as a pressure delivery device for continuing to supply the anesthetic agent gel back through the inflation port 66 and into the lumen 57 to continue to urge the anesthetic agent gel through the ports 68 against the wall of the urethra. The device 51 is left in place for an appropriate period of time as for example 15 minutes to ensure that the tissue surrounding the urethra and in particular in the area of the prostate has been anesthetized. As soon as this predetermined period of time has elapsed, the balloon 62 is deflated by withdrawing the anesthetic agent gel back through the duckbill valve back into the syringe. After the balloon 62 has been deflated, the device 51 can be readily removed from the urethra without pain to the patient.

Another device incorporating the present invention is the device 71 as shown in FIGS. 6, 7 and 9 which consists of a flexible elongate tubular member 72 formed of an elastomeric material of the same type utilized in the device 51. However, rather than being provided with a single lumen 57 it is provided with a pair of lumens 73 and 74 which extend substantially the entire length of the flexible elongate tubular member 72. The lumen 73 extends through a balloon inflation and deflation port 76 for inflating a balloon 62 of the type hereinbefore described mounted on the distal extremity of the flexible elongate tubular member 72. The inflation and deflation lumen 73 is connected to a fitting 81 of a conventional type which includes a valve for connection to a conventional syringe (not shown). The lumen 74 serves as an anesthetic agent gel delivery lumen and has its proximal extremity connected into another fitting 82 also of a conventional type which includes for example a duckbill valve and is adapted to be connected to another syringe for supplying anesthetic agent gel to the lumen 74. A plurality of longitudinally and circumferentially spaced apart ports 86 are provided in the member 72 and open into the lumen 74 and are provided for distributing the anesthetic agent gel in the manner hereinbefore described. The ports 86 can have any desired configuration as for example circular or oval and can be sized in the same manner as the ports 68.

The device 71 can be utilized in a manner similar to the devices hereinbefore described with the principal difference being that a separate lumen is provided for inflating the balloon. Thus, the balloon 62 can be inflated with a suitable liquid as for example a saline solution to desired size. After the balloon 62 has been inflated and the member 72 pulled back to anchor and seat the balloon in the bladder outlet, the anesthetic agent gel can be introduced from another syringe through the lumen 74 and through the ports 86, after which the penis can be clamped to the catheter in the manner hereinbefore described to ensure that the anesthetic agent gel is retained within the urethra and is uniformly distributed along the length and circumference of the urethra to cause infusion of the anesthetic agent into the surrounding tissue to anesthesize the tissue. After an appropriate period of time as for example 15 minutes, the clamp from the penis can be removed, the balloon 62 deflated and the device 71 removed from the urethra. Thereafter the following medical procedure as for example a TUNA procedure can be performed.

Still another embodiment of a device incorporating the present invention is the device 91 shown in FIG. 9 which consists of a flexible elongate tubular member 92 formed of an elastomeric material of the type hereinbefore described. The tubular member 92, however, differs from the tubular members hereinbefore described in that the outer surface 93 thereof is provided with a helical ridge 94 extending proximally from the balloon 62 forming helical dams which circumscribe the flexible elongate tubular member for a suitable distance as for example from approximately 1 inch to 5 inches proximal of the balloon 62. The member 92 is provided with a lumen 96 extending from the proximal extremity to the distal extremity. A balloon inflation port 97 is provided which is in communication with the lumen 96 and opens into the balloon 62 for inflating and deflating the same. The ridges 94 as shown can be substantially semicircular in cross section and can be spaced apart a suitable distance as ranging from ½ to 1 centimeter extending longitudinally of the member 92. The ridges can have a suitable height as for example 2 to 3 millimeters. In general, it is desired that the ridges have a height and have a spacing such that the wall 101 forming the urethra 102 in tissue is supported and does not come into engagement with the outer surface 93 of the member 92. At least one port 106 is provided in the member 92 in communication with the lumen 96 to permit the anesthetic agent gel to pass from the lumen 96 and to enter into the helical recess 107 formed between the helical ridges 94 to permit the anesthetic agent gel to helically traverse the length of the tubular member 92 to cause a uniform distribution of the anesthetic agent gel throughout the length of the tubular member 92 and ensuring that the anesthetic agent gel engages the urethral wall 101 throughout the length of the same.

The use of the device 91 is very similar to that hereinbefore described. When utilizing the device and inserting it into the urethra, the device can be covered with a lidocaine gel and then inserted into the urethra until the balloon 62 has been advanced into the bladder. The balloon 62 can then be inflated with the use of a syringe introducing the anesthetic agent gel into the lumen 96 to inflate the balloon 12. After inflation of the balloon, the balloon is seated in the bladder outlet and the penis and catheter are clamped. The anesthetic agent gel under pressure from the balloon 62 passes through the port 106 and through the helical recess 107 formed between the helical ridge 94 to ensure the anesthetic agent gel comes into contact with substantially all portions of the urethral wall to anesthetize the urethral wall and the surrounding tissue. After an appropriate period of time, the penis clamp can be removed, the balloon 62 deflated and the device 101 removed after which the desired medical procedure to thereafter be accomplished can be performed.

Still another embodiment of a device incorporating the present invention is the device 111 as shown in FIG. 10 consisting of a flexible elongate tubular member 112 formed of the same elastomeric material hereinbefore described in conjunction with device 51. A balloon 62 of the type hereinbefore described is mounted on the distal extremity and is inflated through a port 97 in communication with a lumen 96. In this embodiment of the invention, the helical space rather than being provided between helical ridges is formed by a helical recess 116 extending through the outer surface 113 into the body of the tubular member 112. As shown, the helical recess 116 is semicircular in cross section. The port 106 opens into the helical recess 116 and is used for supplying the anesthetic agent gel to the helical recess 116 when the anesthetic agent gel is supplied to inflate the balloon 62 in the manner hereinbefore described. Thus it can be seen that the anesthetic agent gel is supplied along the length of the urethra and retained in the urethra by the balloon in the bladder outlet and by the clamp on the penis at the other extremity of the urethra. After an appropriate period of time, the penis clamp can be removed and the balloon deflated and the device 111 removed after which the medical procedure to be thereafter performed can be undertaken.

From the foregoing it can be seen that there has been provided a device and a method for delivery of an anesthetic agent gel for topical application to a wall forming a passage in tissue as for example to the urethral wall. In all of the embodiments of the invention, care is taken to ensure that there is a uniform distribution of the anesthetic agent substantially throughout the length of the urethra and particularly in the vicinity of the prostate when utilized in connection with the human male anatomy. Care is also taken to ensure that the anesthetic agent gel cannot leak from the urethra into the bladder.

It also should be appreciated that although the present device has been described potentially in connection with the use in a TUNA procedure, it can be readily used for other procedures in which a device is to be inserted into a passage as for example systoscopes, endoscopes, and the like. The device is constructed in such a manner so it can be readily manufactured so that it can be made inexpensively, permitting disposal after one time use.

What is claimed:

1. A device for delivering a topically applied anesthetic agent to a wall forming a passage in tissue comprising a flexible elongate cylindrical member having proximal and distal extremities, said member being sized so that it can be inserted into the passage, a balloon mounted in the distal extremity of the flexible elongate cylindrical member, said member having a lumen extending from the proximal extremity to the distal extremity and a balloon inflation port in the member in communication with the balloon and the lumen in the member for inflating and deflating the balloon and means including at least one port proximal of the balloon for supplying an anesthetic agent through the port to the wall along at least the distal extremity of the member for a sufficient period of time to anesthesize the wall and the tissue surrounding the wall wherein other medical devices can be inserted thereafter into the passage without substantial pain to the patient.

2. A device as in claim 1 wherein said device includes means for retaining the anesthetic agent within the passage during the time that the member is disposed in the passage.

3. A device as in claim 2 wherein said device has at least a distal extremity thereof formed of an open celled plastic foam material having impregnated therein an anesthetic agent.

4. A device as in claim 1 wherein an anesthetic agent is disposed in the lumen.

5. A device as in claim 3 further including a stiffening member disposed in the flexible elongate cylindrical member and extending from the proximal extremity to the distal extremity.

6. A device as in claim 5 wherein said stiffening member is formed of a solid medical grade plastic.

7. A device as in claim 3 further including a release liner enclosing the member and serving to retain within the member the anesthetic agent impregnated in the member.

8. A device as in claim 1 wherein the at least one port proximal of the balloon includes a plurality of ports proximal of the balloon.

9. A device as in claim 1 wherein said at least one port proximal of the balloon is in communication with the lumen used for inflating the balloon.

10. A device as in claim 1 wherein an additional lumen is provided in the member extending from the proximal extremity to the distal extremity and wherein said at least one port is in communication with said additional lumen.

11. A device as in claim 10 wherein said at least one additional lumen includes a plurality of ports distributed longitudinally and circumferentially of the member.

12. A device as in claim 1 wherein said member has an outer surface and wherein a helical ridge is formed on the outer surface extending outwardly from the outer surface and forming a helical space between the ridges and wherein said at least one port opens into the helical space between the ridges.

13. A device as in claim 1 wherein said member is provided with an outer surface, said outer surface having a helical recess formed therein and wherein said at least one port opens into said helical recess.

14. A device as in claim 10 further including first and second fittings mounted on the proximal extremity of the member with the first fitting being in communication with the first-named lumen and the second fitting being in communication with the additional lumen.

15. A method for delivering an anesthetic agent to be topically applied to the wall forming a passage in tissue with the use of a device comprising a flexible elongate cylindrical member having a predetermined length and size to be able to be introduced into the passage, the device carrying means for delivering an anesthetic agent for uniform distribution over the outer surface of the member, comprising inserting the device into the passage, controlling the anesthetic agent so that it does not leak from the passage, retaining the member within the passage for a predetermined period of time to anesthesize the wall and the tissue surrounding the wall, removing the member from the passage and thereafter performing an additional medical procedure utilizing a device which must be inserted into the passage.

16. A method as in claim 15 wherein the device has an outer surface which includes an open celled porous foam impregnated with an anesthetic agent liquid.

17. A method as in claim 15 wherein the patient has a bladder and wherein the passage is a urethral passage that extends into the bladder and wherein the device is provided with an inflatable balloon mounted on the distal extremity of the device and wherein the controlling step includes the step of inserting the device into the passage until the balloon is disposed in the bladder and thereafter inflating the balloon and withdrawing the device so that the balloon seats in the bladder outlet to seal the urethral passage from the bladder to prevent leakage of anesthetic agent liquid from the passage into the bladder.

18. A method as in claim 17 wherein the controlling step includes the step of applying a clamp to the penis to clamp the penis and the device to prevent anesthetic agent liquid from seeping from the urethral passage out of the penis and into the bladder, further comprising the step of removing the clamp after a predetermined period of time and deflating the balloon and removing the device from the urethral passage.

19. A method as in claim 17 further including the step of inflating the balloon utilizing the anesthetic agent liquid and utilizing the inflated balloon to continue to apply pressure to the anesthetic agent gel to continue to urge, the anesthetic agent gel into contact with the wall forming the urethral passage.

20. A method as in claim 17 further including the step of inflating the balloon independently of supplying an anesthetic agent liquid.

21. The method of claim 15 wherein the means for delivering an anesthetic agent for uniform distribution over the outer surface of the member includes at least one port proximal of the balloon for supplying an anesthetic agent through the port to the wall.

* * * * *